US008600689B2

United States Patent
Orihashi et al.

(10) Patent No.: US 8,600,689 B2
(45) Date of Patent: Dec. 3, 2013

(54) AUTOMATIC ANALYZER

(75) Inventors: Toshihide Orihashi, Hitachinaka (JP);
Yoshimitsu Takagi, Hitachinaka (JP);
Mikio Kasama, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 219 days.

(21) Appl. No.: 11/518,176

(22) Filed: Sep. 11, 2006

(65) Prior Publication Data
US 2007/0072299 A1   Mar. 29, 2007

(30) Foreign Application Priority Data
Sep. 12, 2005   (JP) .................. 2005-263165

(51) Int. Cl.
*G06F 19/00*   (2011.01)

(52) U.S. Cl.
USPC ........................................... 702/85

(58) Field of Classification Search
USPC ........... 702/22, 23, 24, 25, 27, 30, 31, 32, 85, 702/86
See application file for complete search history.

(56) References Cited

U.S. PATENT DOCUMENTS

| | | | |
|---|---|---|---|
| 4,627,014 A * | 12/1986 | Lo et al. ...................... | 702/25 |
| 4,678,755 A * | 7/1987 | Shinohara et al. ............. | 436/43 |
| 5,083,283 A * | 1/1992 | Imai et al. ................... | 702/25 |
| 5,424,212 A | 6/1995 | Pinsl-Ober et al. | |
| 5,492,831 A * | 2/1996 | Ranger ........................ | 436/50 |
| 5,550,053 A * | 8/1996 | Salpeter ...................... | 436/8 |
| 6,080,364 A * | 6/2000 | Mimura et al. ............... | 422/67 |
| 6,269,276 B1 | 7/2001 | Akhavan et al. | |
| 6,275,150 B1 * | 8/2001 | Mandler et al. .............. | 340/525 |
| 6,579,717 B1 * | 6/2003 | Matsubara et al. ........... | 436/50 |
| 6,601,006 B2 * | 7/2003 | Carpenter et al. ........... | 702/104 |
| 6,823,277 B1 * | 11/2004 | Poulsen ...................... | 702/85 |
| 6,846,457 B1 * | 1/2005 | Tokiwa et al. ............... | 422/67 |
| 6,984,527 B2 * | 1/2006 | Miller ......................... | 436/180 |
| 7,381,370 B2 * | 6/2008 | Chow et al. .................. | 422/64 |
| 2005/0037502 A1 | 2/2005 | Miller | |
| 2005/0071110 A1 * | 3/2005 | Davis .......................... | 702/123 |

FOREIGN PATENT DOCUMENTS

JP   2000-187037   7/2000

* cited by examiner

*Primary Examiner* — Bryan Bui
(74) *Attorney, Agent, or Firm* — Mattingly & Malur, PC

(57) ABSTRACT

An automatic analyzer includes a function in which the measured data of a quality control sample is compared with reference maximum and minimum values of measured data of the quality control sample. When the measured data is out of the range between the reference maximum and minimum values, re-measurement for calibration is recommended to a user who can easily confirm the recommendation on an operation screen and request the re-measurement.

6 Claims, 6 Drawing Sheets

FIG. 3

| ANALYSIS ITEM | TARGET MEANS VALUE | TARGET SD | REFERENCE MINIMUM VALUE | REFERENCE MAXIMUM VALUE |
|---|---|---|---|---|
| ALB | 10.0 | 0.5 | 9.0 | 11.0 |
| Ca | 5.0 | 0.4 | 4.2 | 5.8 |
| TP | 6.0 | 0.4 | 6.2 | 6.8 |

QUALITY CONTROL SAMPLE : C1    LOT NO. : 0001   (301, 302, 303)

TARGET MEANS VALUE : [ 10.0 ] — 305
TARGET SD : [ 0.5 ] — 306
⬇ — 307
REFERENCE MINIMUM VALUE : [ 9.0 ] — 308
REFERENCE MAXIMUM VALUE : [ 11.0 ] — 309

[ UPDATE ] — 310            [ STORE ] — 304

FIG. 4

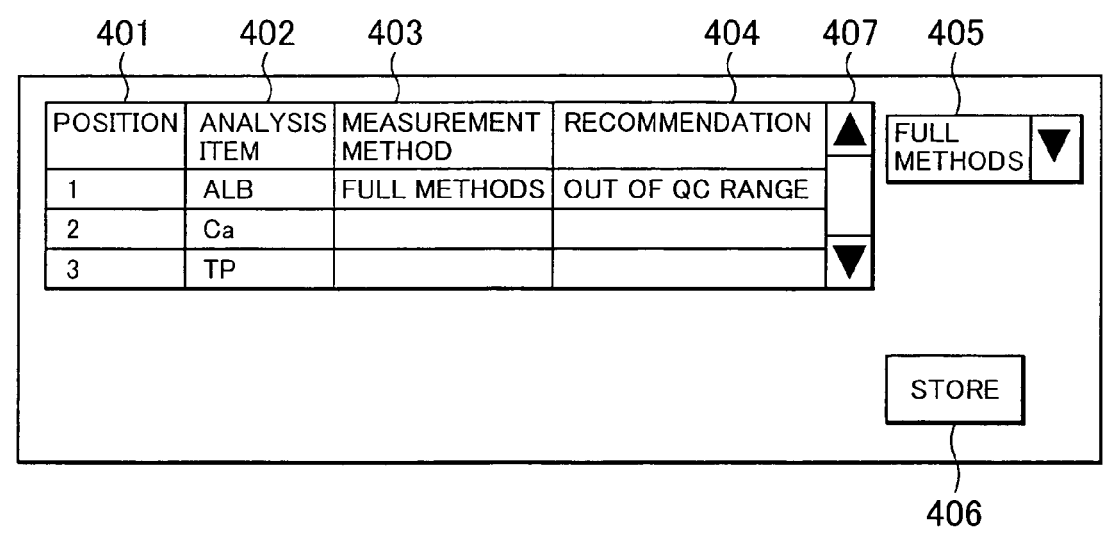

| POSITION | ANALYSIS ITEM | MEASUREMENT METHOD | RECOMMENDATION |
|---|---|---|---|
| 1 | ALB | FULL METHODS | OUT OF QC RANGE |
| 2 | Ca | | |
| 3 | TP | | |

FULL METHODS ▼

STORE

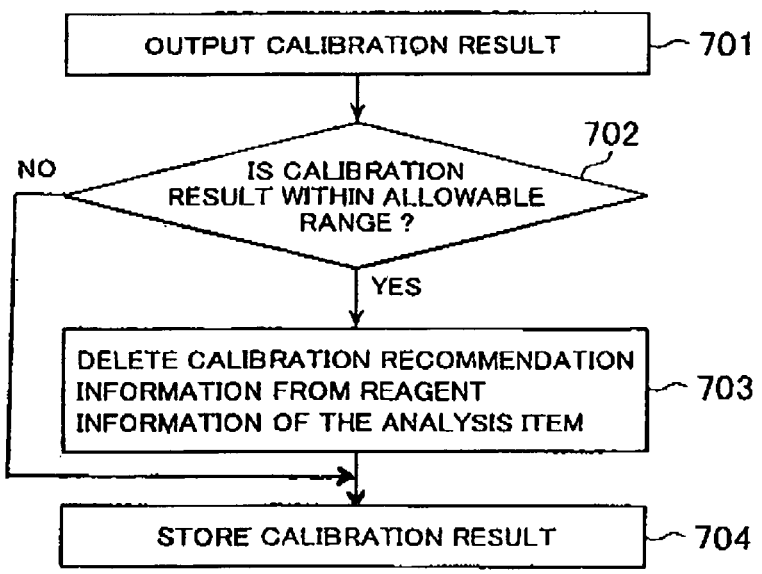

AUTOMATIC ANALYZER

BACKGROUND OF THE INVENTION

The present invention relates to an automatic analyzer which performs the qualitative and quantitative analysis of a biological sample such as blood and urine and, in particular, to an automatic analyzer which performs the quality control of analysis results and an analyzer using measured data of a quality control sample.

DESCRIPTION OF THE RELATED ART

An automatic analyzer, which performs the qualitative and quantitative analysis of a biological sample such as blood and urine by using reagent that specifically reacts on a measurement object component within the biological sample and changes its own physical properties, has been spread mainly in large hospitals and medical laboratories due to high measurement reproducibility and a high processing ability. In such the automatic analyzer, so-called quality control, for periodically measuring a sample (quality control sample) which density is known in advance, is performed in order to determine whether or not the measured result is reliable.

The conventional automatic analyzer is provided with a display function capable of easily confirming whether or not the measured data of a quality control sample is within a target range, as described in JP-A-2000-187037.

SUMMARY OF THE INVENTION

In the conventional automatic analyzer, when the measured data of a quality control sample is out of the target range, in general, a user determines a measure from the user's past experience based on the measured data of the quality control sample and calibration results etc. However, it is supposed that an operator inexperienced in the operation of the automatic analyzer may not be able to determine the measure. Further, in the case of measuring the quality control sample, there is a problem that the setting of the measurement is troublesome.

An object of the present invention is to provide an automatic analyzer which provides a means capable of executing the re-measurement of a calibration or a quality control sample easily with respect to a reagent of an analysis item as to which the measured data of a quality control sample is out of the range between reference maximum and minimum values set in advance so that even an operator inexperienced in the operation of the automatic analyzer can quickly perform a measure for the quality control and a highly reliable analysis can be realized continuously.

In order to attain the aforesaid object, an automatic analyzer according to the present invention is configured in the following manner. First, there is provided with a means for setting and storing determination parameters which are used to determine the measured data of a quality control sample. The determination parameters are information for discriminating the quality control sample (for example, name of the quality control sample), a range between reference minimum and maximum values (a coefficient as to a control SD (Standard Deviation)) and calibration methods (combination patterns of standard samples used in the calibration measurement).

Next, a value obtained by multiplying the control SD of the quality control sample registered in the analyzer by a coefficient of the range between reference minimum and maximum values is added to/subtracted from a control means value to determine the reference minimum and maximum values used for determining the measured data of the quality control sample. The reference minimum and maximum values can be set by an operation unit and stored in a memory unit. Further, in a system where the information as to the control average value and the control SD of the quality control sample can be registered via an external input medium (for example, a bar code), the reference minimum and maximum values are automatically calculated at the time of the registration and stored in the memory means.

When the quality control sample is measured and the measured data is outputted, firstly, it is determined whether or not the measured data is data to be employed as the quality control data. In this determination, alarm information of data to be outputted together with the measured data is employed. For example, as to the measured data in which an alarm such as the shortage of the sample not suitable to be employed as the quality control data, the determining processing using the reference minimum and maximum values is not executed.

When the measured data to be employed as the quality control data is outputted, the determining processing using the reference minimum and maximum values described below is executed.

As the determining processing, first, the determination parameters and the reference minimum and maximum values are read from the memory means. When the quality control sample is set as the determination parameter of the analysis item, the measured data of the quality control sample is compared with the reference minimum and maximum values.

When the measured data of the quality control sample is out of the range between the reference minimum and maximum values, as to the reagent used in the measurement of the analysis item, the recommendation information of the calibration measurement is stored in the memory means together with the reagent information (a reagent lot No. and a sequential No. of the reagent).

In contrast, when the measured data of the quality control sample is within the range between the reference minimum and maximum values, the recommendation information of the calibration measurement stored in the memory means is deleted.

The measured data of the quality control sample subjected to the determination using the reference minimum and maximum values is stored in the memory unit in the order of being outputted.

In the case of performing the calibration measurement, when the calibration result being outputted is within an allowable range and satisfies a calibration curve update condition, the recommendation information of the calibration measurement stored in the memory means is deleted.

An operation unit includes a display and input means which can confirm the reagent information of the analysis item as to which the re-measurement of the calibration is recommended and also can request the measurement of the calibration easily as to the recommended reagent. Further, there is provided with a display and input means which can confirm the measured data of the quality control sample being out of the range between the reference minimum and maximum values and also can easily perform the re-measurement of the quality control sample.

According to the present invention, there is provided with a displaying and measurement requesting function for easily performing the re-measurement of a calibration or a quality control sample with respect to a reagent of an analysis item as to which the measured data of the quality control sample is out of the reference range between the reference maximum and minimum values set in advance. Thus, the analyzer is realized which can continuously realize a highly-reliable analysis and improve the measurement accuracy. Further, the analyzer according to the present invention attributes to the reduction of work load of a user.

BRIEF DESCRIPTION OF THE DRAWINGS

FIG. 3 is a diagram showing an example of a screen for displaying the target values for the measured data of the quality control samples;

FIG. 4 is a diagram showing an example of a screen for a calibration measurement request;

FIG. 7 is a flow chart showing the updating processing of calibration recommendation information at a time of executing a calibration.

DESCRIPTION OF THE PREFERRED EMBODIMENTS

The present invention is characterized by including an operation screen for setting for setting in advance reference maximum and minimum values for determining the measured data of a quality control sample and an operation screen for recommending and displaying the re-measurement of a calibration with respect to a reagent of an analysis item as to which the measured data of a quality control sample is out of a reference range. Further, the present invention preferably includes an operation screen capable of executing easily the re-measurement of a calibration or a quality control sample with respect to a reagent of the analysis item.

The present invention will be explained in detail by using drawings.

Hereinafter, an embodiment of the present invention will be explained with reference to the accompanying drawings.

Figure 1:
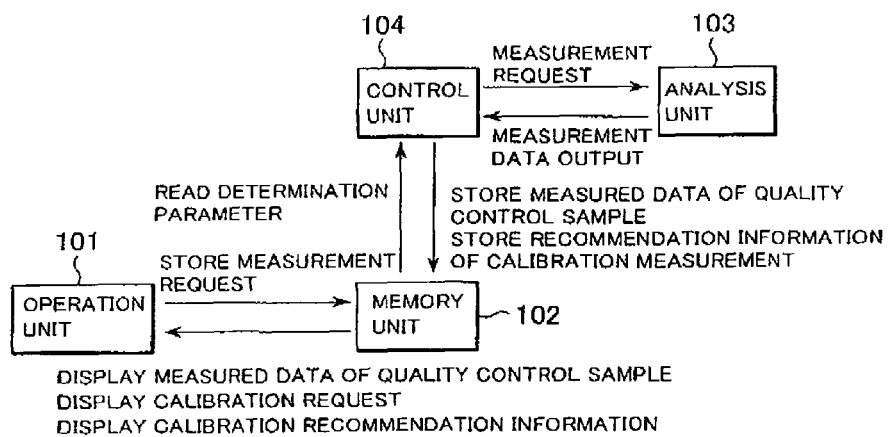
FIG. 1 is a schematic diagram showing the basic configuration of an analyzer according to the embodiment of the present invention.

FIG. 1 is a diagram showing the configuration of an automatic analyzer according to the embodiment of the present invention. An operation unit 101 is configured by a key board or a CRT, and is arranged to display the measured data of a quality control sample, a calibration request and recommendation information and to perform an operation such as a request for measuring a quality control sample and a calibration. A memory unit 102 is configured by a hard disk driving device etc. and stores the measured data of a quality control sample, the recommendation information of calibration measurement and so on. An analysis unit 103 is arranged to pipet and measure a sample.

A control unit 104 controls the memory unit 102 and performs the determining processing of the measured data and so on.

Figure 2:
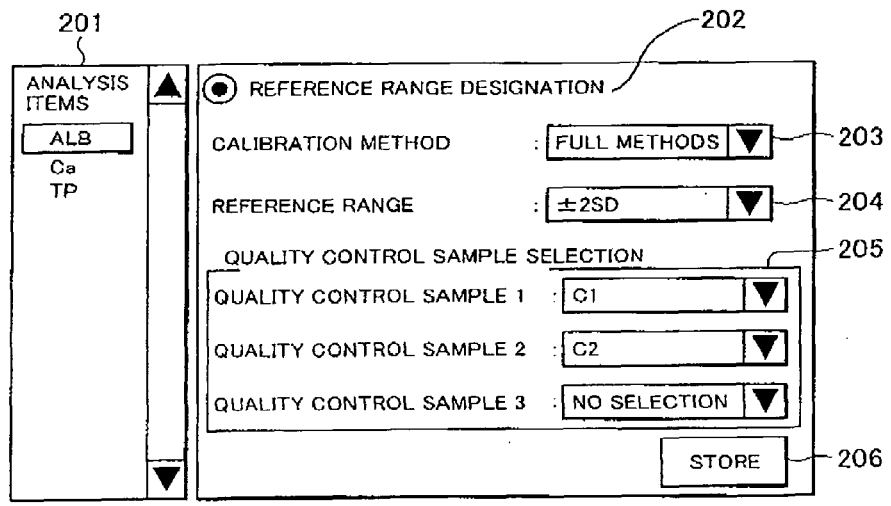
FIG. 2 is a diagram showing an example of a screen for setting determination parameters for the measured data of quality control samples.

FIG. 2 shows a screen arrangement for setting determination parameters for the measured data of quality control samples with respect to analysis items registered in the analyzer. A reference numeral 201 depicts a list of the analysis items registered in the analyzer. The determination parameters stored in the memory unit 102 are displayed in correspondence to the analysis item selected by the list 201. Then, the determination parameters will be explained in detail. A reference range designation 202 is a button for selecting the validation or invalidation of the setting of the reference range of the quality control sample. The setting of the reference range is made valid only when the reference range designation 202 is selected. A calibration method 203 is a menu for selecting the combination of standard samples used upon executing the calibration. A reference range 204 is a menu for setting as to what coefficient is to be multiplied to a control SD 306 shown in FIG. 3 so that the multiplied control SD is used as a reference range in order to determine the measured data of a quality control sample. A selection 205 is a menu for setting a quality control sample used for determining the reference range. In the example of the menu 205, three kinds of the quality control samples can be set at the maximum. The setting contents of the button 202 and the menus 203 to 205 can be changed on the operation unit. When a store button 206 is selected, the contents of the button 202 and the menus 203 to 205 thus changed are stored in the memory unit 102.

FIG. 3 shows an example of a screen arrangement for setting a target value, reference maximum value, a reference minimum value etc. of the quality control sample registered in the analyzer. A quality control sample 301 depicts the name of the quality control sample. A lot number 302 depicts the lot No. of the quality control sample. Values set at the analysis item selected by a target value display list 303 are displayed at a target means value 305, a target SD 306, the reference minimum value 308 and the reference maximum value 309. These values can be edit on the operation unit. A calculation button 307 is used to automatically calculate the reference minimum value 308 and the reference maximum value 309 in accordance with the following expressions (1) and (2) by using, the target means value 305, the target SD 306 and the reference range 204.

(reference minimum value 308)=(target means value 305)−(target SD 306)−(reference range 204)  (1)

(reference maximum value 309)=(target means value 305)+(target SD 306)−(reference range 204)  (2)

For example, in the case of FIGS. 2 and 3, as to the analysis item ALB, the target means value 305 is 10. 0, the target SD 306 is 0.5 and the reference range 204 is in a range between +2SD and −2SD. Thus, the reference minimum value 308 is 9.0 according to the expression (1) and the reference maximum value 309 is 11.0 according to the expression (2).

When an update button 310 is selected, the set values 305, 306, 308 and 309 are reflected on the target value display list 303. When the store button 304 is selected, the set values displayed at the target value display list 303 are stored in the memory unit 102.

FIG. 4 shows an example of a screen arrangement for the calibration measurement request. In a calibration request list 407, the setting positions of reagents are displayed at the column of a position 401, analysis items are displayed at the column of an analysis item 402, a calibration method recommended or requested for analysis is displayed at the column of a measurement method 403, a reason why the calibration request is recommended (for example, a calibration has not been measured yet, a QC measurement value is out of the range between the reference maximum and minimum values) is displayed at the column of a recommendation 404. In the example of FIG. 4, the reagent ALB as the analysis item is set at the setting position 1 and the full methods are set by the button 405 as the calibration method as to this regent. Further, as to this reagent, since the measured data of the quality control sample is out of the range between the reference maximum and minimum values, the recommendation of the calibration measurement is displayed due to the reason of the "out of the QC range". When a store button 406 is selected, the calibration measurement request of the full methods is stored in the memory unit 102 as to the analysis item ALB of the set position 1 in which the calibration measurement is recommended. Thus, when a user merely selects the store button 406 once, all the recommended calibration measurement request is stored in the memory unit 102 with respect to all the reagents as to which the calibration measurement is recommended.

Figure 5:
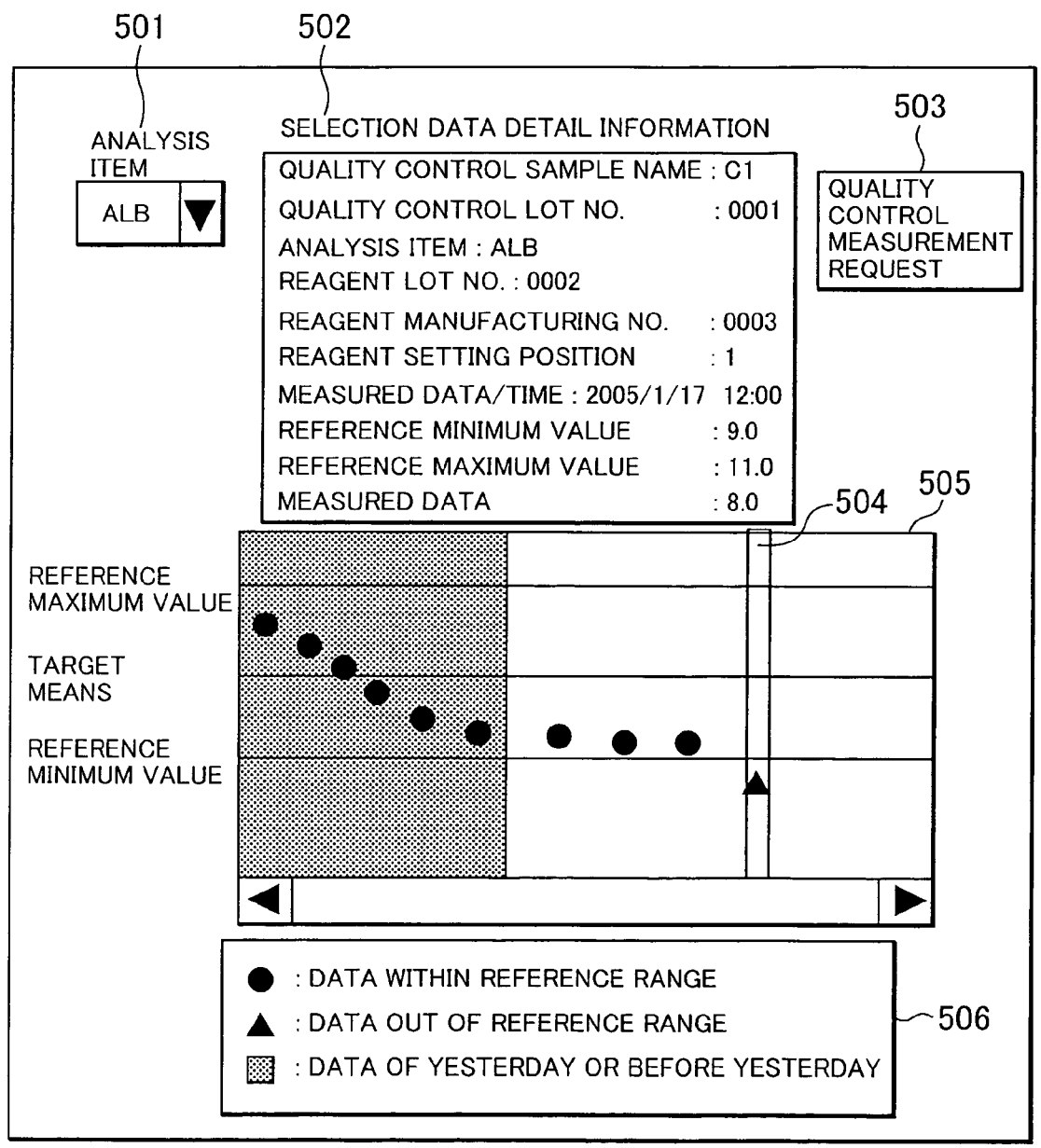
FIG. 5 is a diagram showing an example of a screen for displaying quality control measured data.

FIG. 5 shows an example of a screen displaying the quality control measured data. An analyst item list 501 is a list for selecting the analysis items registered in the analyzer. According to this list, one or all of the analysis items can be designated. When one of the analysis items is selected, the data of the quality control samples as to this selected analysis item having been measured is displayed on a measured data display area 505 in a time-sequence manner. In contrast, when all of the analysis items are selected, the measured data of the quality control samples as to all the analysis items registered in the analyzer is displayed on the measured data display area 505 in a time-sequence manner. A user can select each of the respective measured data by using a cursor 504, whereby the detailed information of the selected data is displayed on a measured data (selection data) detail information area 502.

The measured data display area 505 displays the target means value 305 and the reference line of each of the reference minimum value 308 and the reference maximum value 309. A data lower than the reference minimum value 308 or higher than the reference maximum value 309 is displayed out of a range between these reference lines. As shown in a remark 506, since data within the range between the reference minimum value and the reference maximum value is represented by a sign difference from that of data out of the range, a user can easily specify the measured data out of the range. Further, as shown in a remark 506, when the background design of the measured data display area 505 is differentiated between the measured data of today and the measured data of yesterday or before yesterday, the measured data to be treated today can be easily specified. When a quality control measurement request button is pushed, the measurement request for the quality control sample is made as to the combination of the quality control sample and the reagent used for the analysis of the measured data selected by the cursor 504 and stored in the memory unit 102.

Figure 6:
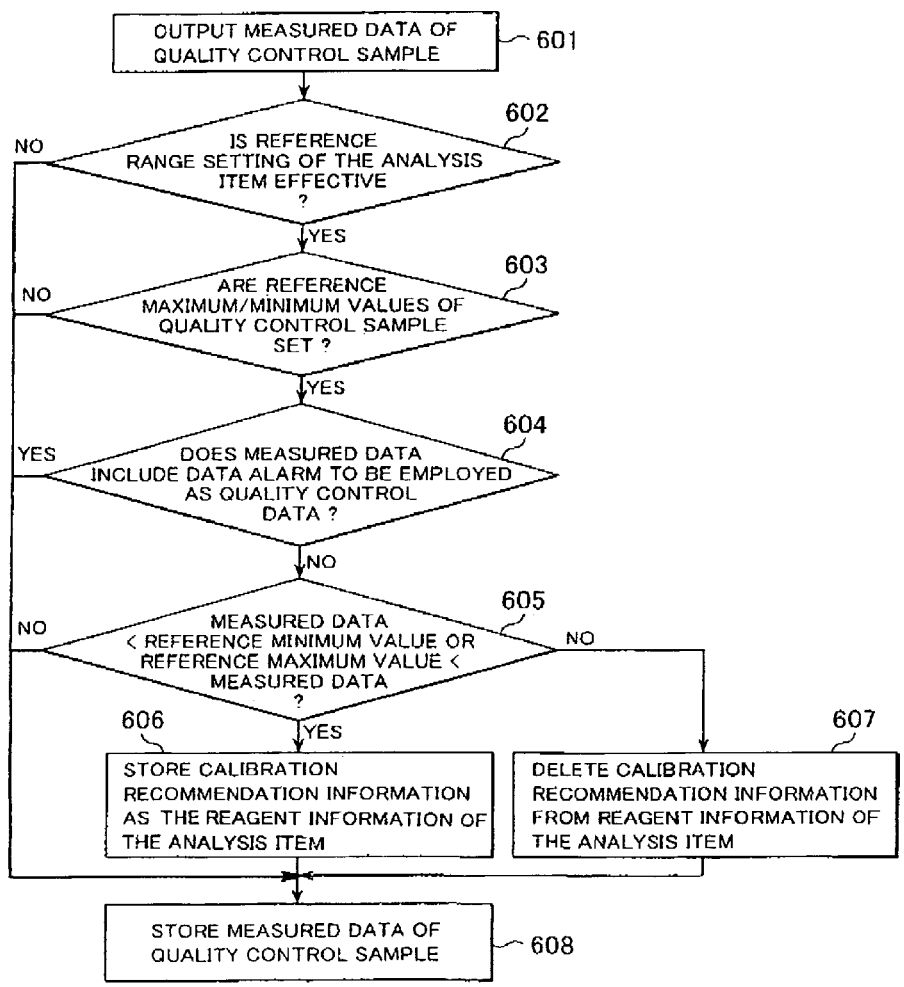
FIG. 6 is a flow chart showing the updating processing of calibration recommendation information at a time of measuring the quality control sample.

FIGS. 6 and 7 show flow charts of the updating processing of the recommendation information displayed at the column of the recommendation 404.

FIG. 6 is a flow chart showing the processing at the time of the measurement of the quality control sample. When the measured data of the quality control sample is outputted (step 601), it is determined whether or not the reference range designation 202 of this analysis item is effective (step 602) When the reference range designation 202 is effective, it is checked whether or not the reference minimum value 308 and the reference maximum value 309 are set (step 603). When both the reference minimum value 308 and the reference maximum value 309 are set, it is determined whether or not the measured data contains a data alarm (such as the shortage of the sample) which should not be employed as the quality control data (step 604). When the data alarm is not outputted, the measured data is compared with the reference minimum and maximum values (step 605). As a result of the determination of the step 605, when the measured data is out of the range between the reference minimum and maximum values, the recommendation information of the calibration is set as to the reagent information of this analysis item and stored in the memory unit 102 (step 606). In contrast, when the measured data is within the range between the reference minimum and maximum values, the recommendation information of the calibration set as to the reagent information of this analysis item is deleted and stored in the memory unit 102 (step 607). These recommendation information of the calibration can be confirmed on the screen of FIG. 4. The re-measurement of the calibration can be requested by selecting the store button 406. After the execution of the steps 606 and 607, the measured data is stored in the memory unit 102 (step 608). The measured data can be confirmed on the screen of FIG. 5. The re-measurement of the quality control sample can be requested by selecting the quality control measurement request button 503.

FIG. 7 is a flow chart showing the processing at the time of the measurement of the calibration. When the calibration result is outputted (step 701), it is determined whether or not the calibration result is within the allowable range (step 702). When the calibration result is within the allowable range, the recommendation information of the calibration set as to the reagent information of this analysis item is deleted and stored in the memory unit 102 (step 703). The recommendation state of the calibration can be confirmed on the screen of FIG. 4.

What is claimed is:

1. An automatic analyzer comprising:
quality control sample setting means for setting selected quality control samples from amongst a plurality of quality control samples for each of a plurality of analysis items registered in said automatic analyzer, said selected quality control samples being used for judging whether a measurement result for one of the analysis items is within a predetermined reference range, said selected quality control sample having a known component;
reference range setting means for setting a reference range for each of the selected quality control samples set by said quality control sample setting means, said reference range being defined by a reference minimum value and a reference maximum value; and
calibration setting means for, when measurement data of one of said quality control samples related to one of said analysis items is not within the reference range defined by said reference minimum value and said reference maximum value, setting one of a plurality of calibration methods which are combinations of standard samples used in the calibration measurement of a reagent of one of said analysis items, and said calibration setting means displaying a reason why a calibration request is recommended.

2. An automatic analyzer according to claim 1, wherein, when said calibration method is set as to the reagent of one of said analysis items by the calibration setting means, instructing a request for measurements of said quality control samples collectively.

3. An automatic analyzer according to claim 1, wherein, when a result of execution of a calibration method set by the calibration setting means is within the reference range and satisfies a calibration curve update condition, deleting the calibration request.

4. An automatic analyzer according to claim 1, further comprising:
memory means that stores measurement data of the quality control samples; and
display means for displaying the measurement data of the quality control samples having been measured by designating the analysis item and displaying the measured data within the reference range and the measured data out of the reference range in a distinguishable manner.

5. An automatic analyzer according to claim 4, wherein measurement data is displayed by the display means in a distinguishable manner by date.

6. An automatic analyzer according to claim 5, wherein an instruction button for instructing a request for quality control measurement is displayed by the display means.

\* \* \* \* \*